United States Patent [19]

Purdy et al.

[11] Patent Number: 5,797,882
[45] Date of Patent: Aug. 25, 1998

[54] ARTERIAL CATHETER AND CATHETER/ NEEDLE ASSEMBLY WITH IMPROVED FLOW CHARACTERISTICS AND METHOD FOR ITS USE

[75] Inventors: Edmund Robert Purdy, Fruit Heights, Utah; Charles W. Daugherty, Jamestown, Ohio

[73] Assignee: Becton Dickinson and Company, Franklin Lakes, N.J.

[21] Appl. No.: 702,084

[22] Filed: Aug. 23, 1996

[51] Int. Cl.$^6$ ............................................. A61M 5/00
[52] U.S. Cl. ........................ 604/164; 604/280; 604/282
[58] Field of Search ................................ 604/164, 264, 604/280, 282

[56] References Cited

U.S. PATENT DOCUMENTS

| | | | |
|---|---|---|---|
| 1,596,754 | 8/1926 | Moschelle | 604/282 |
| 4,257,422 | 3/1981 | Duncan | 604/282 X |
| 4,790,831 | 12/1988 | Skribiski | 604/282 |
| 4,840,623 | 6/1989 | Quackenbush | 604/280 |
| 5,300,032 | 4/1994 | Hibbs et al. | 604/164 |
| 5,496,292 | 3/1996 | Burnham | 604/282 |
| 5,496,294 | 3/1996 | Hergenrother et al. | 604/282 |
| 5,593,394 | 1/1997 | Kanesaka et al. | 604/282 |
| 5,601,603 | 2/1997 | Illi | 606/213 |
| 5,647,846 | 7/1997 | Berg et al. | 604/93 |

FOREIGN PATENT DOCUMENTS 6-158957  1/1996  Japan.

*Primary Examiner*—Corrine M. McDermott
*Attorney, Agent, or Firm*—Eric M. Lee

[57] ABSTRACT

An arterial catheter includes an elongate tube having a sidewall with an inside surface and an outside diameter. The catheter has a proximal end, an open distal end with a tip portion, and a hollow bore with an inside diameter. There is a hub attached to the proximal end of the catheter that is in fluid communication with the hollow bore. The inside surface of the hollow bore has a plurality of inward projections disposed longitudinally from the proximal end to the distal end. The tip portion has at least one hole through the sidewall into the bore. The catheter sidewall outside diameter is tapered distally from the hole to the open distal end and the inward projections on the inside surface of the bore are substantially diminished in the tip portion.

17 Claims, 11 Drawing Sheets

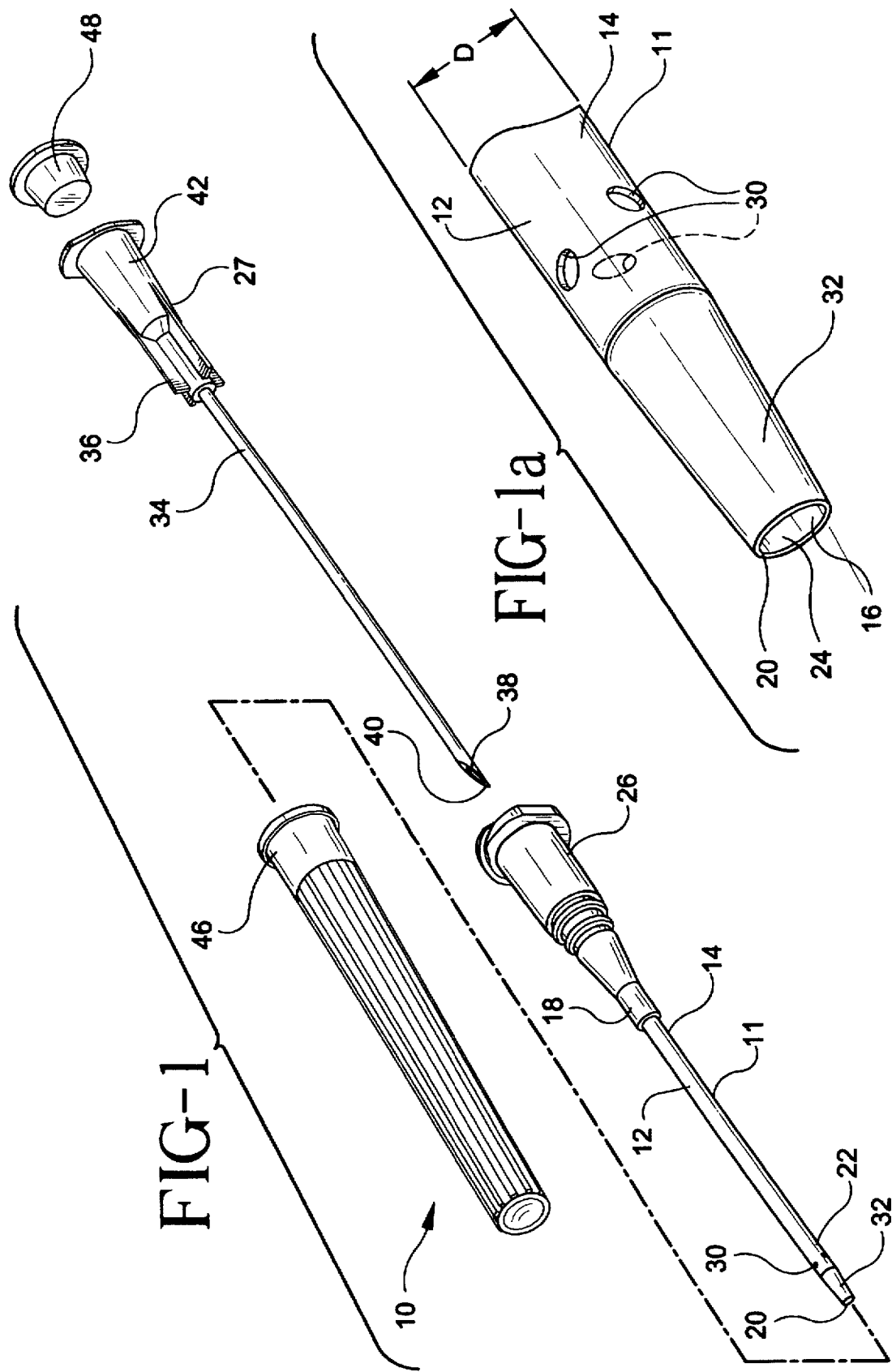

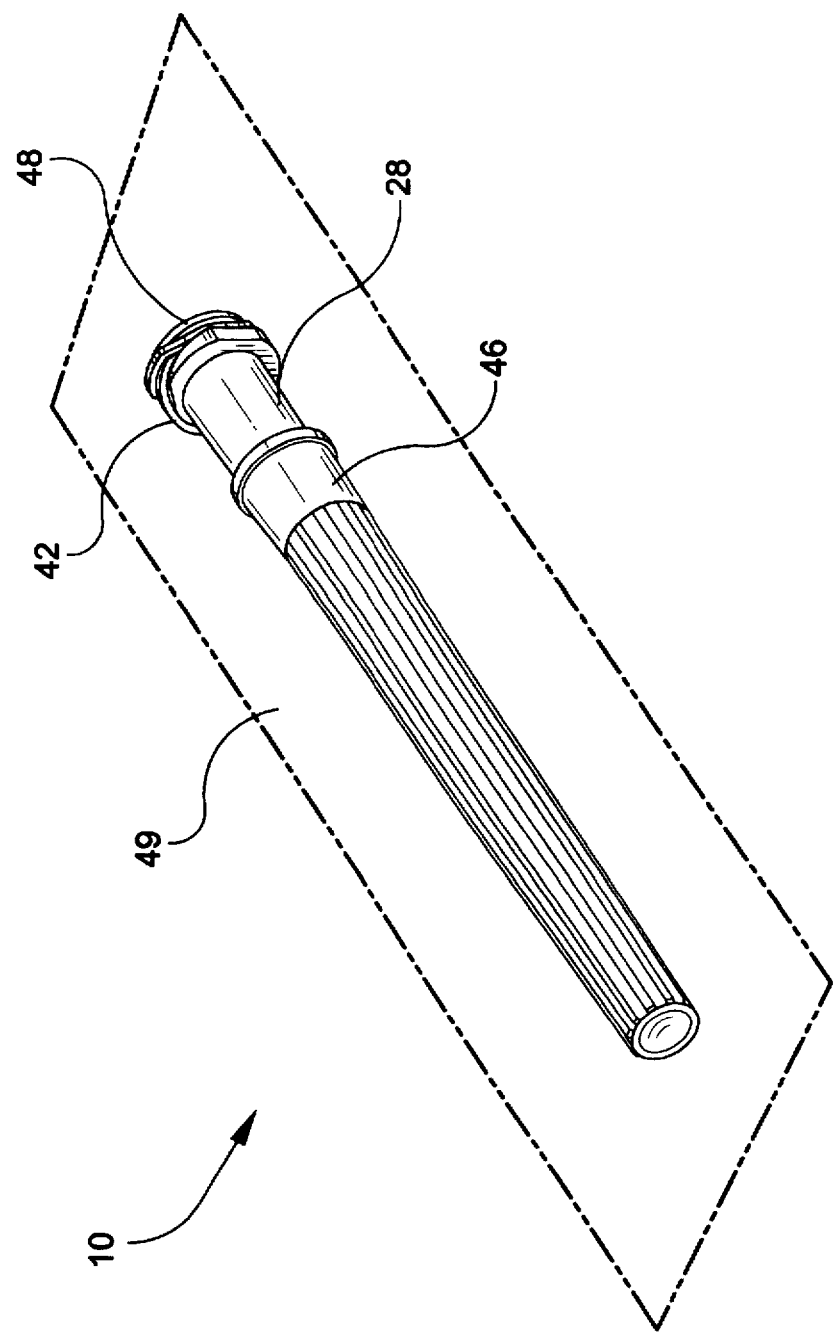

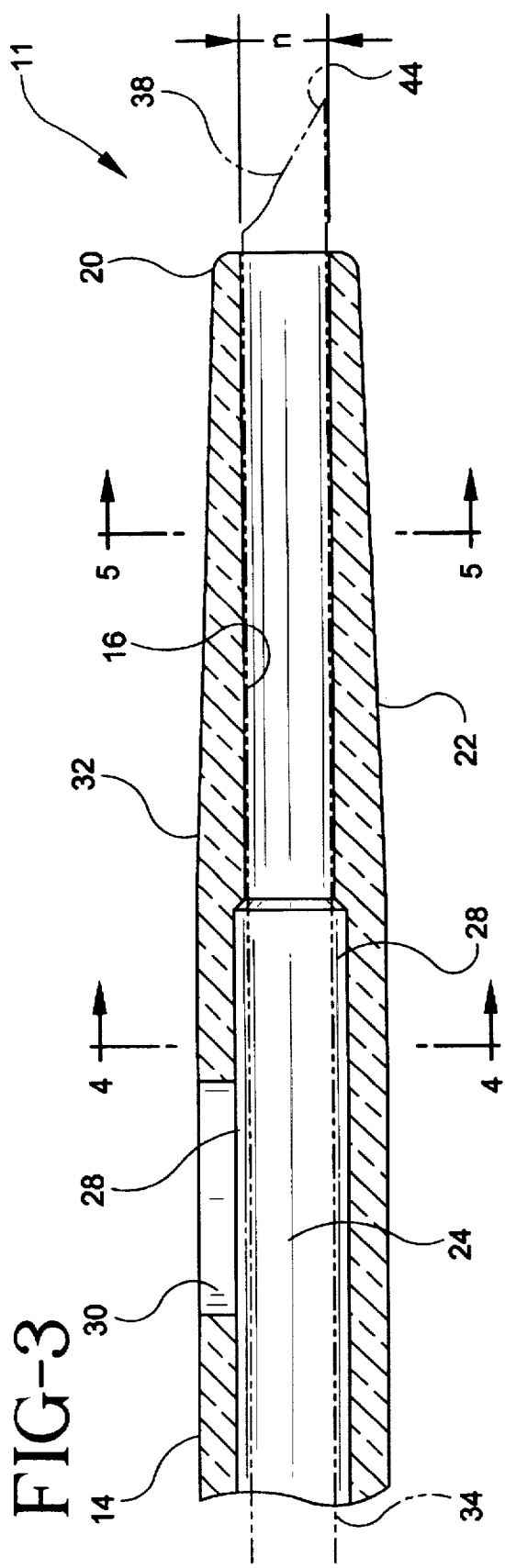
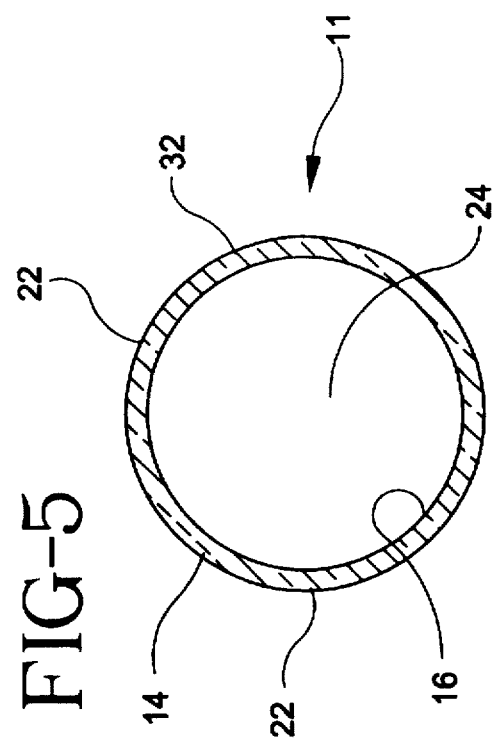
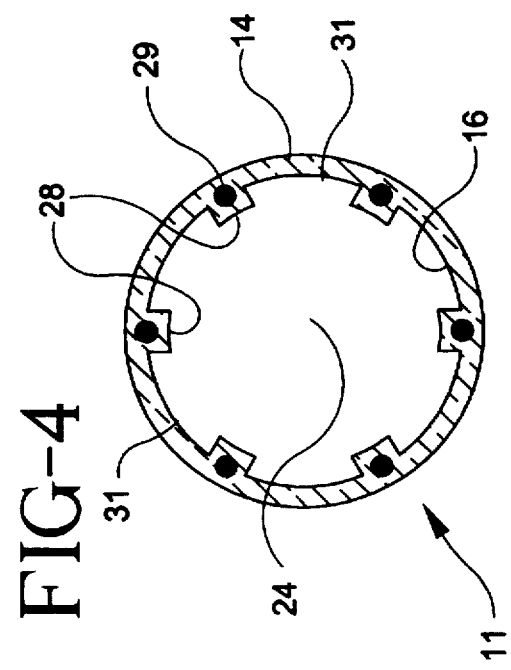

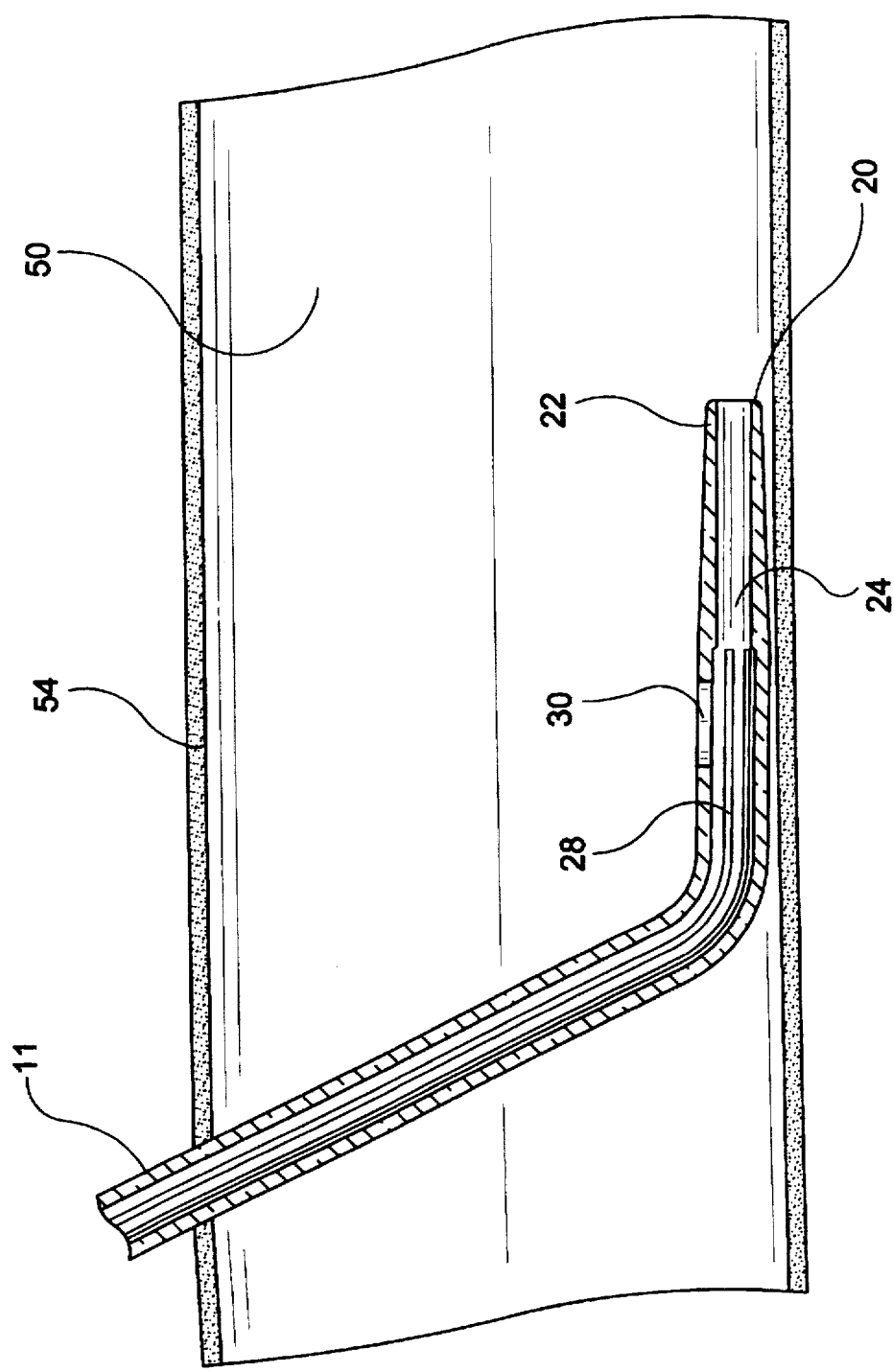

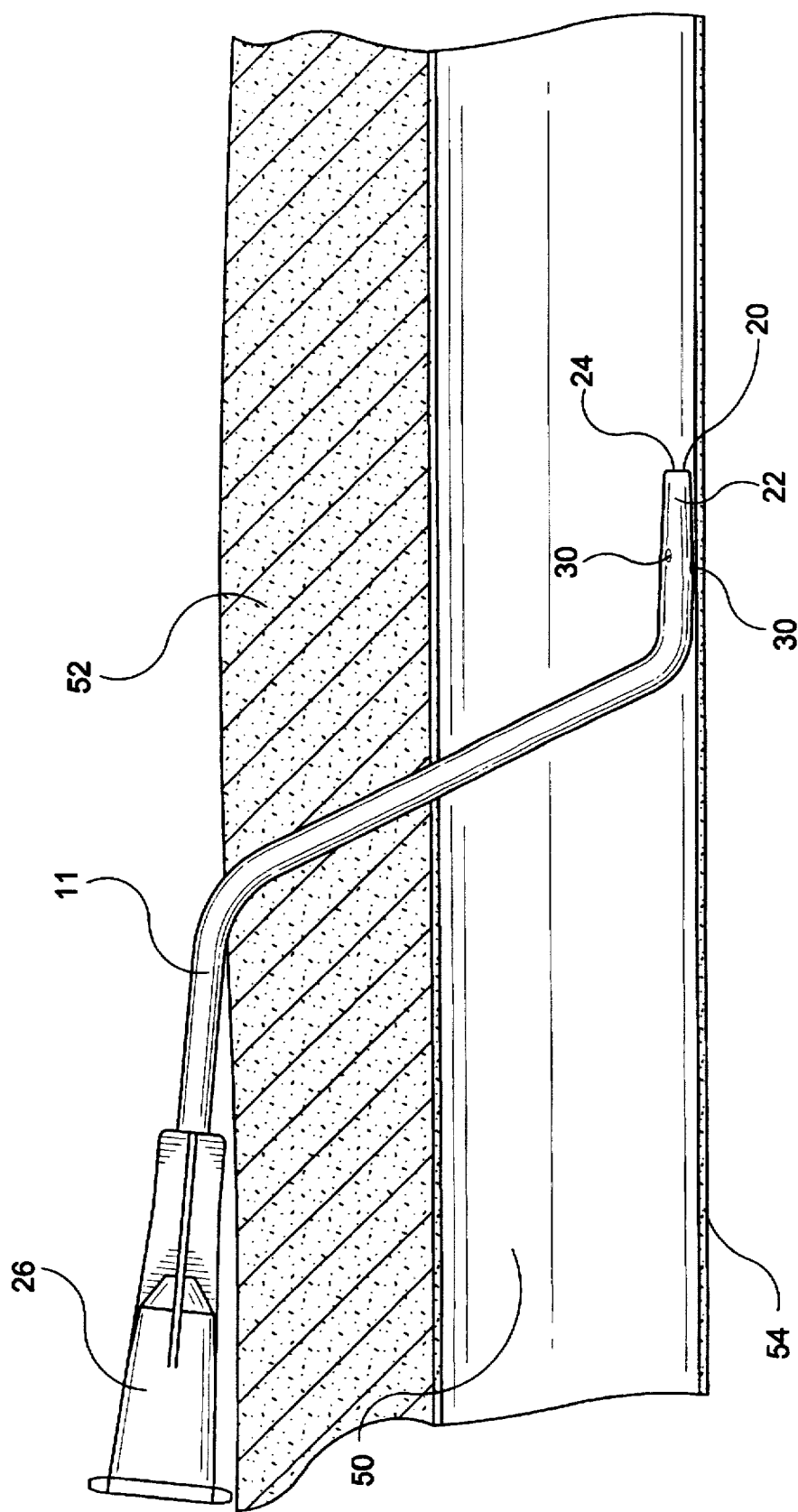

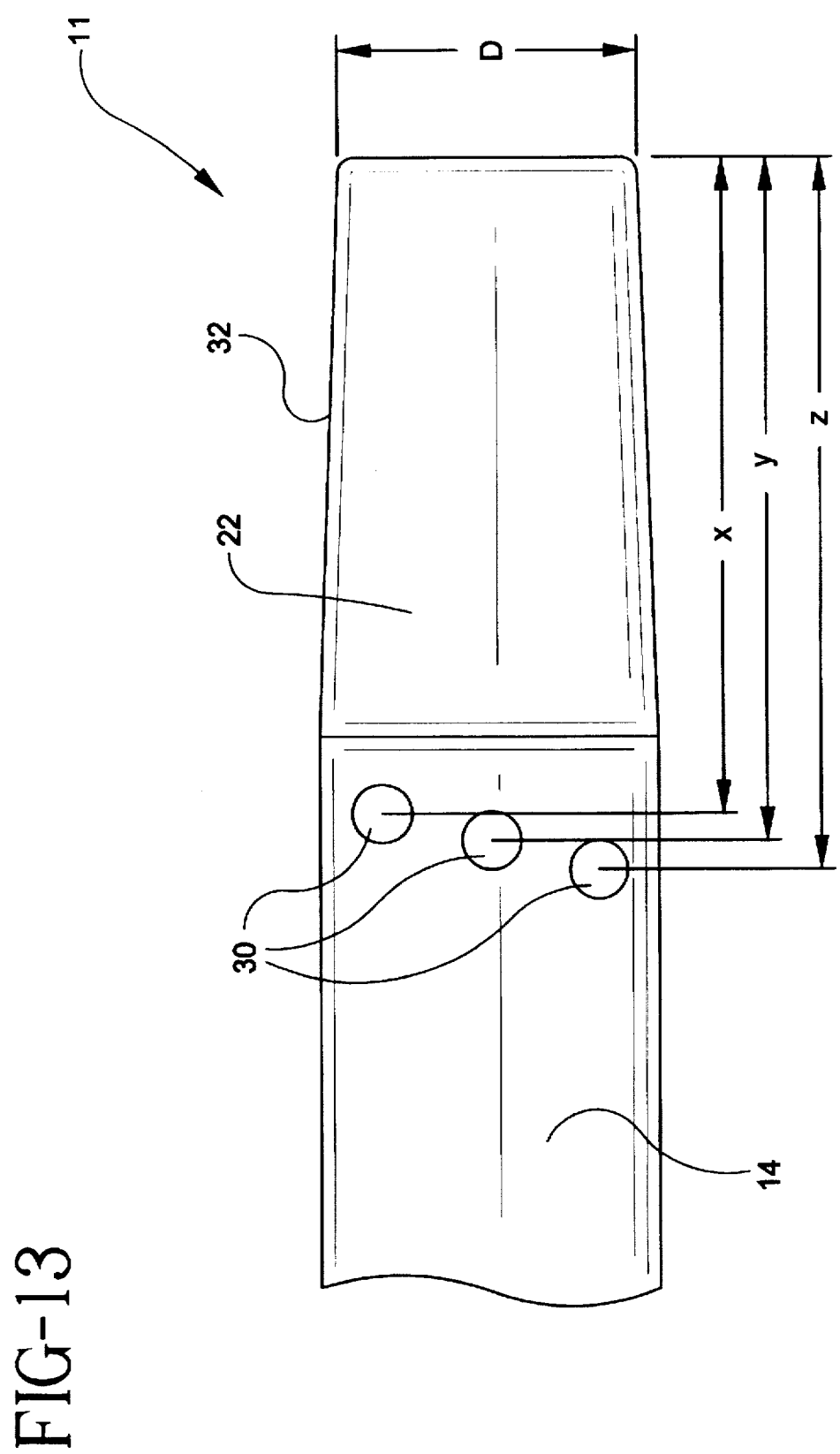

ARTERIAL CATHETER AND CATHETER/ NEEDLE ASSEMBLY WITH IMPROVED FLOW CHARACTERISTICS AND METHOD FOR ITS USE

FIELD OF INVENTION

This invention relates to intravascular catheters and more particularly to an over-the-needle arterial catheter with provisions to maintain fluid pathway patency.

BACKGROUND

An intravascular catheter is generally a flexible small diameter tube inserted into a patient's blood vessel to allow withdrawal or addition of fluid. Typically, a practitioner places the catheter by locating a target blood vessel for the placement, then pierces the patient's skin and the blood vessel wall with an inserter needle, uses the needle to lead the catheter into the vessel and then removes the needle, leaving the catheter in the vessel. Catheters may be inserted into blood vessels either through the bore of the inserter needle or over the outside of the inserter needle. In this disclosure, catheters that are inserted over-the-needle are described. Additionally, a convention is followed in this disclosure using the term "proximal" to refer to the portion of the device closest to the practitioner and the term "distal" for the portion of the device toward the patient or away from the practitioner.

Over-the-needle catheters are generally supplied already mounted on an inserter needle in a sterile, ready-to-use, unit package. In its simplest form, the over-the-needle catheter generally resembles one tube slidably fit within another tube, the flexible catheter being outermost with a sharp beveled point inserter needle slidably fit within the catheter bore so that the sharp distal inserter needle point projects beyond a gently tapered distal end of the catheter. In placement of these over-the-needle catheters, the needle, with the catheter outside, is held by the practitioner, generally with the point bevel face up, longitudinally aligned with the target blood vessel, then placed into the vessel.

Catheters are placed both in veins and in arteries. When the target blood vessel is a vein, the needle is then inserted at a shallow angle through the patient's skin into the blood vessel. The practitioner then often determines that the needle is properly positioned within the blood vessel by allowing a small quantity of the patient's blood to flow through the hollow needle bore, impelled by the patient's blood pressure, so that the small quantity of blood can be seen at the rear of the needle. This practice of using the patient's blood to signal proper placement of needle within the target vessel is termed "flashing or flashback." The flashing step has the purpose of confirming that the catheter is properly inserted into the blood vessel. Once the proper placement is confirmed, the practitioner applies finger pressure to the vessel over the distal tip of the needle and the catheter to occlude further blood flow, withdraws the needle and attaches a fluid handling device to the catheter hub.

When an artery is the target blood vessel, the practitioner generally inserts the needle at a steeper angle than is the usual practice for venous placement, because arteries are deeper in the patient's tissue. The practitioner uses the flash to confirm that the needle point is in the target vessel. The catheter is advanced into the vessel and the needle is withdrawn. The presence of a second flash in the catheter hub is indicative of the catheter being in the blood vessel. Often, a blood sample is analyzed to confirm that the catheter needle is placed in the desired artery, not a vein. To obtain a blood sample, several manipulative steps may be required. Alternatively, a practitioner may choose to allow a sufficient amount of the patient's blood to escape to confirm that the pulsatile blood flow characteristic of arterial blood is present.

An "ideal" arterial catheter has two conflicting physical property requirements. A high degree of stiffness is desirable to facilitate placement of the catheter in the artery. However, once placed, since the placement angle is relatively steep when compared to the placement angle of a venous catheter, a stiff catheter is more likely to cause damage to the inside wall of the artery opposite the penetration site. If an arterial catheter is formed from a compliant soft material, it is less likely to cause damage to the patient's blood vessel A soft arterial catheter is useful for administration of fluids to a patient, but if the soft catheter is used for withdrawal of blood samples or for placement of a pressure sensor, a compliant soft material may collapse at the tip when suction is applied to withdraw a sample or become occluded where it bends, either at the vessel or on the patient's skin.

Because of the likelihood of occlusion by bending or by collapse, most commercially available arterial catheters are formed from polytetrafluoroethylene (PTFE) and are somewhat stiff. There are also kink resistant tubes used in the medical arts for oxygen tubes and certain types of catheters. Some commercially available oxygen tube sets have formed longitudinal ridges within the bore of the tubing, the ridges tend to interfere with each other when the tube is bent or twisted and maintain a flow path through the bore.

U.S. Pat. No. 4,790,831 discloses a torque-control catheter adapted to be inserted in to the cardiovascular system. The catheter has a body formed from a soft outer sheath coextruded over a stiffer core or inner tube having a multi-lobal cross section. The outer portion of the disclosed tube defines a plurality of longitudinally extending ribs that protrude radially outwardly at circumferentially spaced-apart locations on the tube. The inner bore of the disclosed tube is smooth. The patent is silent to the kinking and fluid path occlusion, rather, the disclosure teaches achievement of desired torque control properties for angiography and angioplasty procedures.

Another patent disclosing a catheter with internal structure is U.S. Pat. No. 4,840,623. This patent discloses a medical catheter with a splined internal wall. The patent teaches that the splined wall can be formed as a coextrusion to provide a long catheter that is useful for angioplasty procedures. The patent is silent to occlusion of the bore.

If an arterial catheter were available that had sufficient stiffness to facilitate placement, that softened after placement to substantially reduce trauma to blood vessel walls and was resistant to occlusion from bending and suction, the art of arterial catheterization would be advanced. Such a catheter is disclosed below.

SUMMARY

An arterial catheter of the present invention includes an elongate tube that has a sidewall with an inside surface and an outside diameter. The catheter has a proximal end, an open distal end with a tip portion, and a hollow bore with an inside diameter. There is a hub attached to the proximal end of the catheter that is in fluid communication with the hollow bore. The inside surface of the hollow bore has a plurality of inward projections disposed longitudinally from the proximal end to the distal end. The tip portion has at least one hole through the sidewall into the bore. The catheter sidewall outside diameter is tapered distally from the hole to the open distal end and the inward projections on the inside surface of the bore are substantially diminished in the tip portion.

The inward projections on the inside wall of the bore of the catheter of the invention substantially reduce the possibility of occlusion of the bore when the catheter is bent, because as the bore is collapsed by bending, the inward projections interfere with each other and maintain a pathway for fluid flow. Additionally, the at least one hole through the sidewall provides a pathway for fluid to enter the bore if the tip is occluded. Over-the-needle catheters generally are formed from extruded tubing that has a uniform cross-section. The extruded tubing is cut to the desired length and the distal tip of an over-the-needle catheter is generally formed into a taper to facilitate the entrance of the catheter tubing into a blood vessel. If a catheter is formed from a soft material, the thin tip area is prone to collapse, either from suction or from bending, and substantially prevent fluid flow. Because of the need to avoid collapse and bore occlusion, many current arterial catheters are formed from substantially stiff tubing. In the present invention, while formation of the tapered tip substantially diminishes the inward projections that keep the bore open, the at least one hole in the sidewall of the present invention maintains fluid path patency. The catheter of the invention is thus able to be formed from a softer material. The use of the softer material in catheter of the invention thus substantially eliminates problems associated with damage to the blood vessel opposite the penetration site seen with catheters formed from stiffer materials.

BRIEF DESCRIPTION OF THE DRAWINGS

FIG. 1 is an exploded perspective view of the arterial catheter assembly of the present invention;

FIG. 1a is an enlargement of the tip portion of the arterial catheter from FIG. 1;

FIG. 2 is a perspective view of the arterial catheter assembly from FIG. 1 as assembled and packaged;

FIG. 3 is a longitudinal cross-sectional view of the tip portion of the arterial catheter from FIG. 1a;

FIG. 4 is a lateral cross-sectional view of the arterial catheter of FIG. 3 along the line 4—4;

FIG. 5 is a lateral cross-sectional view of the arterial catheter of FIG. 3 along the line 5—5;

FIG. 11 is a schematic partial cross-sectional view of the arterial catheter of the invention positioned in a blood vessel;

FIG. 12 is a schematic side view of the arterial catheter of the invention positioned in a blood vessel;

FIG. 13 is a laid-open view of the exterior of the tip portion of the arterial catheter of the present invention;

DETAILED DESCRIPTION

Figure 6:
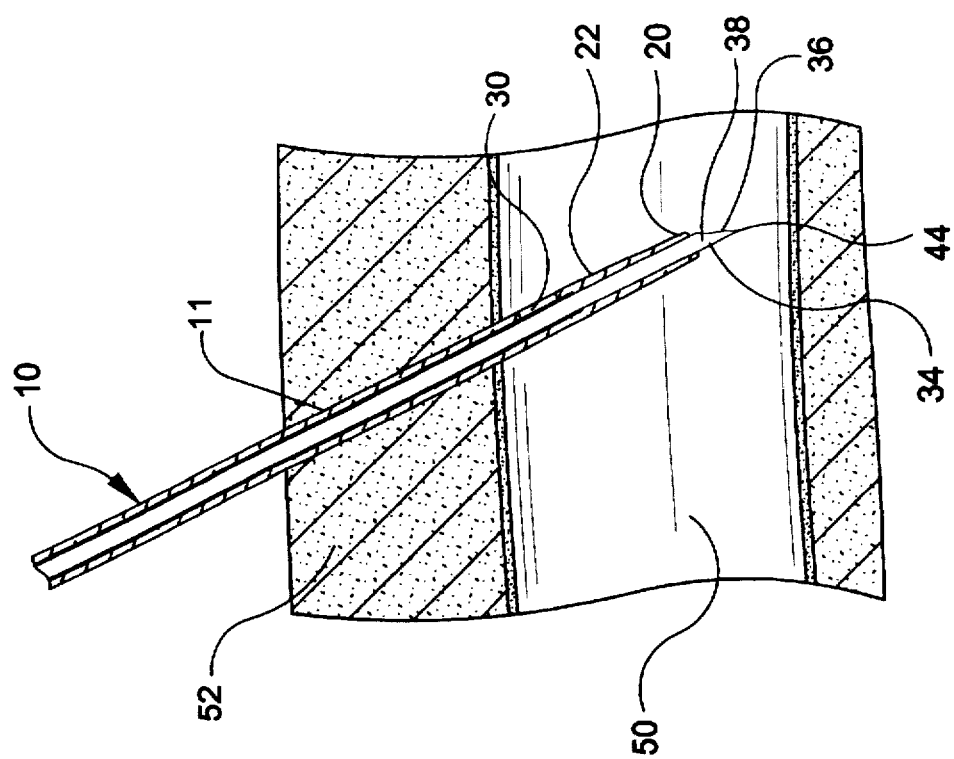
FIG. 6 is a schematic partial longitudinal cross-sectional view illustrating initial placement of the arterial catheter of the invention into a blood vessel.

While this invention is satisfied by embodiments in many different forms, there are shown in the drawings and herein described in detail, preferred embodiments of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1–7 and 10–13, an arterial catheter assembly 10 of the present invention includes an arterial catheter 11 that has an elongate tube 12 with a sidewall 14 that has an inside surface 16 and an outside diameter "D". Arterial catheter 11 has a proximal end 18, an open distal end 20 with a tip portion 22, and a hollow bore 24 with an inside diameter "n". Arterial catheter 11 has a hub 26 attached to proximal end 18 in fluid communication with hollow bore 24. Inside surface 16 of the hollow bore of arterial catheter 11 has a plurality of inward projections 28 disposed longitudinally from proximal end 18 to distal end 20. As shown in FIG. 1a, tip portion 22 has at least one hole 30 through sidewall 14 into bore 24 and also has a taper 32 of sidewall outside diameter "D" distally from adjacent hole 30 to open distal end 20. Taper 32 facilitates entrance of catheter 11 into the patient's blood vessel. Inward projections 28 in bore 24 are substantially diminished on inside surface 16 at tip portion 22.

Assembly 10 also includes an elongate inserter needle 34 with a proximal end 36, a distal end 38, and a passageway 40 therethrough. Inserter needle 34 is sized to fit within inside diameter "n" of bore 24 of arterial catheter 11. Inserter needle 34 has a hub 42 attached at proximal end 36 that is sized to releasably fit within hub 26 of arterial catheter 11 and a sharpened point 44 on distal end 38 of needle 34. Needle 34 has a sufficient length so that sharpened point 44 of needle 34 extends beyond tip portion 22 of catheter 11 when inserter needle 34 is disposed within bore 24 of catheter 11 and needle hub 42 is positioned within catheter hub 26.

Preferably, assembly 10 is supplied with a shield 46 that releasably fits hub 26 and protects arterial catheter 11 with projecting needle point 40. Assembly 10 also preferably includes a porous plug 48 that releasably fits needle hub 42 and allows blood flowing into needle hub 42 to displace air from the needle and hub. As shown in FIG. 2, assembly 10 preferably supplied assembled with shield 46 and porous plug 48 and sealed in a package 49 (shown in phantom). Package 49 is preferably formed from materials substantially resistant to the passage of microorganisms. Package 49 with assembly 10 therein is preferably exposed to conditions sufficient to render any microorganisms therein nonviable and assembly 10 is then considered sterile as long as package 49 is intact.

Referring to FIGS. 3, 4 and 5, preferred arterial catheter 11 has longitudinal inward projections 28 disposed at regular intervals about inside surface 16 of hollow bore 24 of the catheter. When catheter 11 is flexed or bent, inward projections 28 are of sufficient size, preferably extending inwardly from inside surface 16 more than about 0.05 mm, and shaped to engage each other and maintain a fluid flow path through bore 24. Preferably, at least one of inward projections 28 includes a radiopaque material 29 to provide the practitioner the ability to identify the catheter by X-ray. Radiopaque materials such as barium sulfate and the like are suitable radiopacity agents. Arterial catheter 11 may be formed from polymeric materials such as polyvinylchloride, polyethylene, polytetrafluoroethylene, polyurethane and the like. Preferably, arterial catheter 11 is formed by an extrusion process from a hydrophilic polyurethane that softens when exposed to physiological conditions (37° aqueous saline or blood). A more preferred arterial catheter 11 is formed by incorporation of the radiopaque material into a flexible polyester matrix that is co-extruded with the hydrophilic polyurethane so that one of projections 28 includes at least one stripe 29 of substantially radiopaque polyester encapsulated in the polyurethane. The more preferred co-extrusion provides a catheter that softens with physiological exposure that retains dimensional stability and is reinforced by the polyester.

When the radiopaque agent is incorporated as a stripe, several benefits are provided to the catheter. Most common radiopaque agents, when incorporated into a thermoplastic matrix, also render the thermoplastic substantially opaque to light transmission. By providing the preferred radiopacity agent as discrete stripe 29, a longitudinal space 31 between projections 28 retains the optical properties of the polyurethane, and the density of the x-ray image of the material is enhanced over the density of the x-ray image provided by an equivalent amount of radiopacity agent uniformly dispersed through the entire catheter. Preferably, the hydrophilic polyurethane selected for the catheter is substantially transparent, or at least translucent, so that the presence of blood or other fluids in the catheter is visible to the practitioner through sidewall 14 of the catheter.

Figure 7:
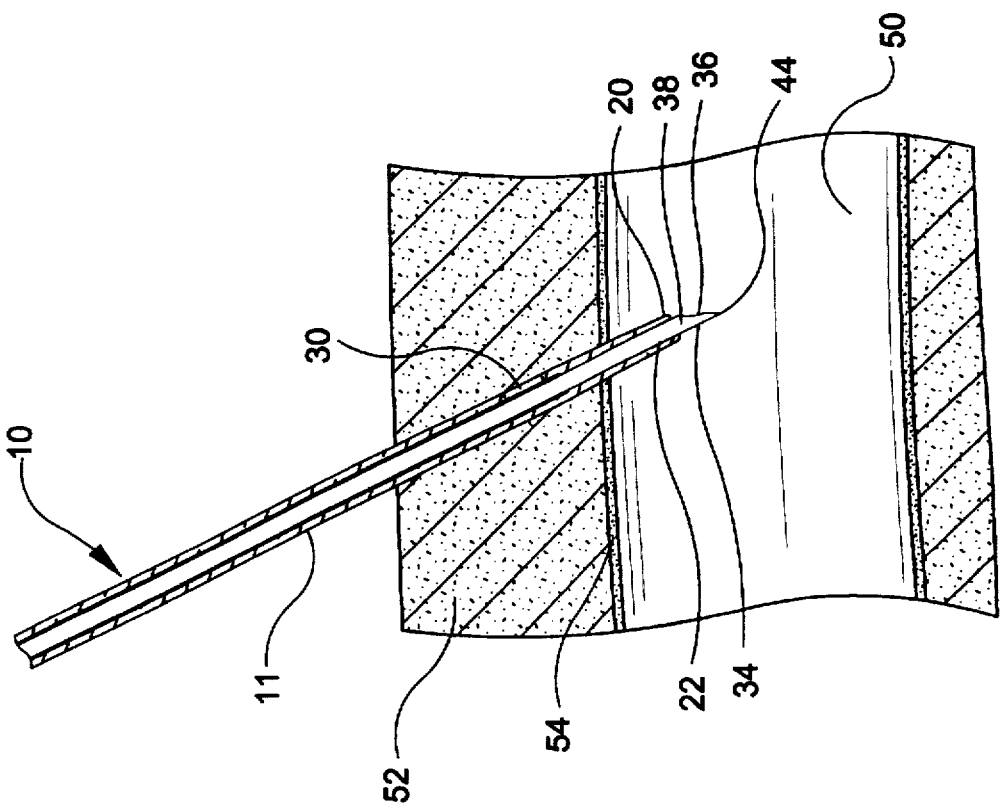
FIG. 7 is a schematic partial longitudinal cross-sectional view, sequential to the view of FIG. 6, illustrating further placement of the arterial catheter of the invention into a blood vessel.

FIGS. 6 and 7 schematically illustrate placement of arterial catheter/needle assembly 10 of the invention in an artery 50. Assembly 10 is introduced at a steeper angle to the patient's skin surface than the angle used for an intravenous catheter, i.e., about sixty-five degrees to about eighty degrees for an arterial puncture compared to about fifteen degrees to about forty degrees for a venipuncture. The practitioner longitudinally aligns assembly 10 with artery 50 and advances distal needle point 36 through the patient's tissue 52 until an artery wall 54 is penetrated. Blood from the artery enters passageway 40 of the needle and is visible at hub 42 of the needle. The practitioner then, as shown in FIG. 7, advances assembly 10 into the artery until hole 30 in the catheter sidewall has entered the artery. The preferred arterial catheter 11 has longitudinal spaces 31 between projections 28 and is formed from a transparent, or at least translucent material. Thus, as soon as hole 30 passes through artery wall 54 blood enters spaces 31 between needle 34 and inside surface 16 of the catheter and is visible through sidewall 14 of the catheter. The ability to visualize the blood between the catherter and the needle provides the practitioner with an indication of proper placement of the catheter. The practitioner then withdraws the needle and continues with the planned procedure.

Figure 8:
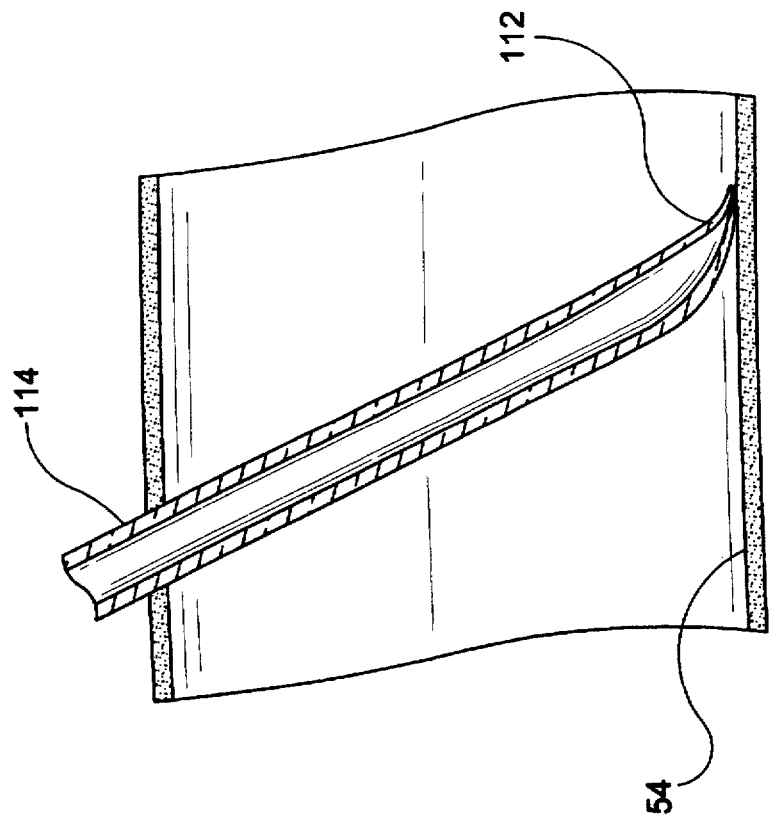
FIG. 8 is a schematic partial longitudinal cross-sectional view illustrating a common substantially rigid arterial catheter in a blood vessel.
Figure 9:
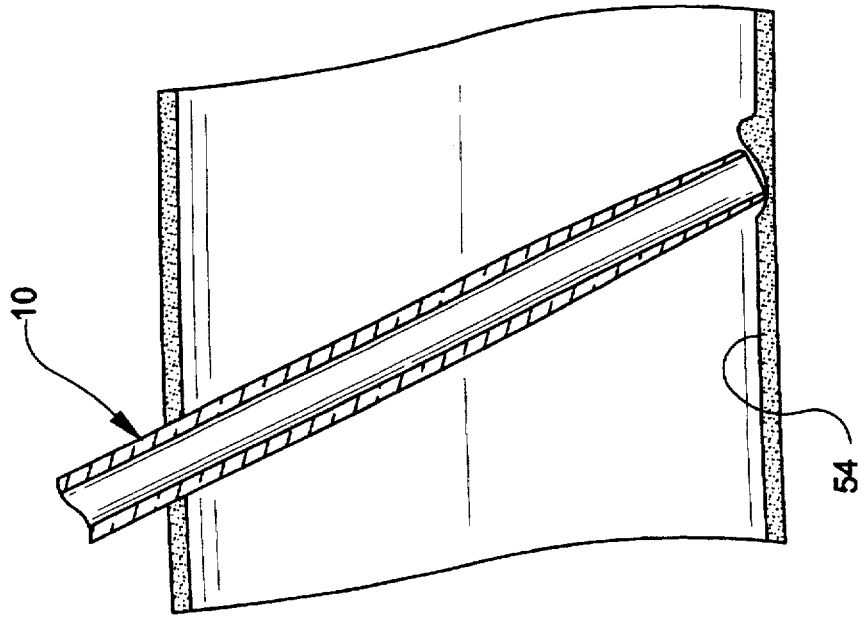
FIG. 9 is a schematic partial longitudinal cross-sectional view illustrating a common soft flexible catheter in a blood vessel.

FIGS. 8 and 9 illustrate problems that may occur with arterial catheters that are formed from a material that is too rigid or too soft. FIG. 8 schematically shows how a stiff arterial catheter 110 may cause trauma to artery wall 54 opposite the penetration site. Trauma to the artery wall may lead to phlebitis or development of other conditions with the artery. FIG. 9 schematically shows how the tip 112 of an arterial catheter 114 formed from a soft material may be collapsed under suction or occluded by collapsing against artery wall 54. When the flow path into the catheter is occluded, withdrawal of samples or fluid communication with a transducer positioned in the catheter may be compromised.

Figure 10:
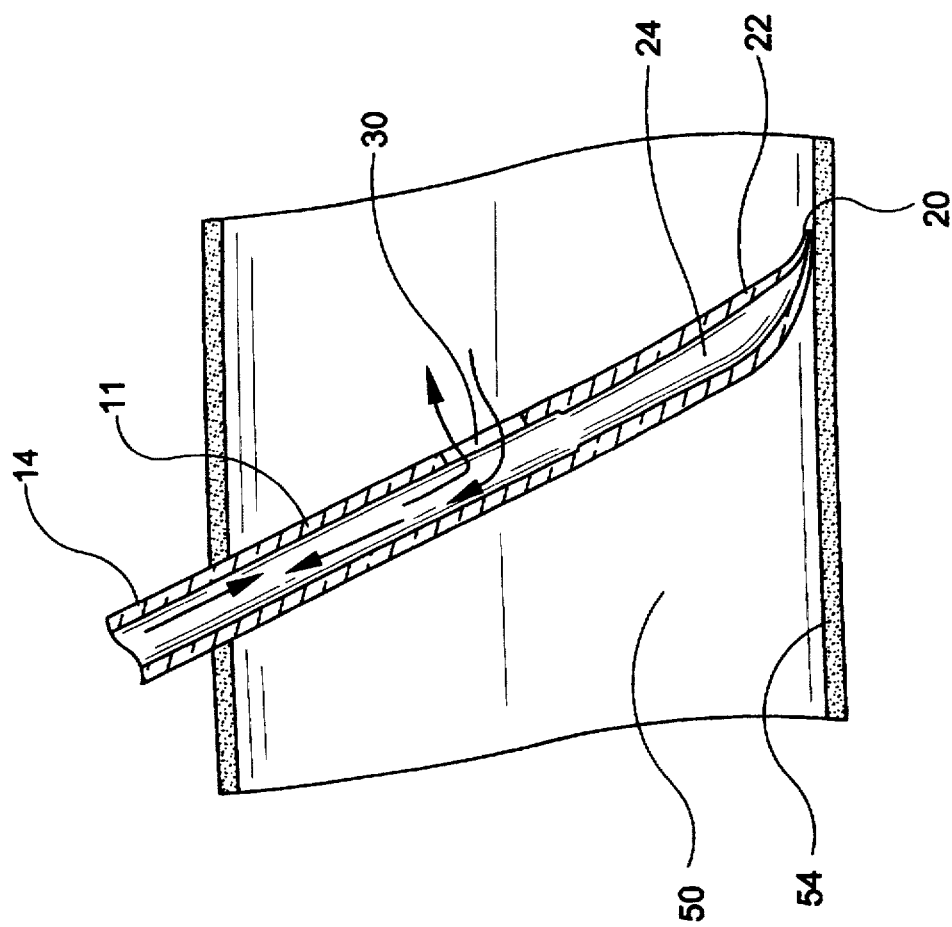
FIG. 10 is a schematic partial longitudinal cross-sectional view of the arterial catheter of the present invention positioned in a blood vessel.

FIG. 10 illustrates arterial catheter 11 of the present invention. Since preferred catheter 11 is formed from a hydrophilic polyurethane that softens after exposure to physiological conditions, tip 22 may be occluded by collapsing against wall 54 of the artery or under suction. When tip 22 is occluded, a fluid path, as indicated by flow arrows, is still available into bore 24 through hole 30 in the catheter sidewall.

FIGS. 11 and 12 show preferred catheter 11 in position in artery 50. Since the preferred arterial catheter softens with exposure to physiological conditions, it readily bends to conform to the artery wall and to be secured to the patient's skin surface. When catheter 11 bends, fluid flow through bore 24 is substantially maintained by contact between projections 28.

FIG. 13 illustrates preferred catheter 11 that has three holes 30 through sidewall 14 spaced about 120 degrees apart. Preferably each hole is between about sixty to about seventy percent of the inside diameter "n". Advantages provided by having the plurality of holes in the sidewall at the tip include providing a higher flow rate through the catheter than would be available just through the open bore end. This is because the total hole area is greater than the area of the open end at the tip since the tip diameter is reduced by the tapering process. Additionally, if the tip is partially or completely occluded, the flow pathway is still available. The preferred plurality of holes also provides for a more dispersed flow of any medicament being added through the catheter. This dispersed flow could substantially reduce the effects of some toxic or highly concentrated medicament upon the sidewalls of the blood vessel.

Preferably, each of holes 30 are different distances, x, y, and z, from distal end 20 of the catheter. Distances x, y, and z are preferably between about 2.8 to about 3.6 times diameter "D" of the catheter. The preferred different distances x, y, and z substantially reduce any weakening of catheter sidewall 14 at tip portion 22 that could occur if all of the holes were the same distance from distal end 20. Taper 32 of the tip portion of the arterial catheter of the invention preferably extends a distance about 3 times diameter "D". Taper 32 at tip portion 22 is preferably formed by thermally softening catheter sidewall 14 with a mandrel positioned into catheter bore 24. The tip portion is then advanced into a tapering and trimming die to form taper 32. The sidewall is preferably then allowed to cool and holes 30 are formed into sidewall 14 against the mandrel in the desired locations. The tapering and trimming operation substantially diminshes interior projections 28 on interior surface 16 of the catheter sidewall.

Table 1 presents the nominal outside diameter corresponding to standard gauge sizes used for hypodermic needles and catheter tubing. The most common catheter sizes used for arterial catheters are 18 gauge to 22 gauge with a length of about five centimeters. These catheters are supplied fitted over needles 20 gauge to 24 gauge. A preferred configuration for assembly 10 of the present invention is a 20 gauge arterial catheter 11 supplied over a 22 gauge inserter needle 34.

TABLE 1

Hypodermic Tubing Size

| Nominal Sizes (Gauge) | Outside Diameter (mm) |
|---|---|
| 30 | 0.30 |
| 29 | 0.33 |
| 28 | 0.36 |
| 27 | 0.40 |
| 26 | 0.46 |
| 25 | 0.51 |
| 24 | 0.56 |
| 23 | 0.64 |
| 22 | 0.71 |
| 21 | 0.82 |
| 20 | 0.90 |
| 19 | 1.08 |
| 18 | 1.27 |
| 17 | 1.50 |
| 16 | 1.65 |

Catheter hub 26 and needle hub 42 are preferably fitted to accept male luer fittings. Catheter hub 26 further is sized and shaped to allow a portion 27 of the exterior of needle hub 42 to fit within it. Needle 34 is fit within arterial catheter 11 to form assembly 10. Catheter hub 26 and needle hub 42 are preferably formed from a thermoplastic material that is substantially transparent or at lest translucent, so that the presence of fluid, particularly blood, is visible in the hub. Thermoplastic materials such as polycarbonate, polyamide and polypropylene are suitable for forming catheter hub 26 and needle hub 42. Hydrophilic polyurethanes that are substantially catalyst and additive free, and are extrudable are suitable for forming tubing for arterial catheter 11 of the invention. Hydrophilic polyurethanes that are sold under the tradename Vialon® by Becton, dickinson and Company, Franklin Lakes, N.J. are preferred as the hydrophilic polyurethane for forming tubing for the arterial catheter of the invention.

Samples of 22 gauge catheter tubing were prepared from polytetrafluorethylene red hydrophilic polyurethane. Test sections of these tubings were subjected to comparative physical tests at ambient and physiologic (37° C./aqueous saline or blood) conditions. The results of these comparative physical tests are shown in Tables 2 and 3.

TABLE 2

Comparative Physical Properties of 22 gauge PTFE and Hydrophilic tubing

| Time | Tensile 37° C. | Tensile amb. | 5% mod. 37° C. | 5% mod. amb. | elong. 37° C. | elong. amb. |
|---|---|---|---|---|---|---|
| Hydrophilic Polyurethane | | | | | | |
| 0 hr | 7507 psi | 8224 psi | 835 psi | 2337 psi | 398% | 293% |
| 4 hr | 6678 psi | 7668 psi | 554 psi | 1107 psi | 258% | 303% |
| PTFE | | | | | | |
| 0 hr | 6737 psi | 6910 psi | 1841 psi | 2005 psi | 157% | 142% |
| 4 hr | 5063 psi | 6060 psi | 1560 psi | 1534 psi | 129% | 130% |

(In Table 2, 37° C. is indicative of physiological conditions)

Referring to Table 2, it is noteworthy that the tensile strength of the hydrophilic polyurethane and the PTFE are similar and substantially unchanged by the test conditions. The 5% modulus values, an indication of compliability, are somewhat comparable for the preferred hydrophilic polyurethane and the PTFE at ambient conditions and before exposure to physiological conditions. The somewhat comparable values for 5% modulus at ambient conditions are indicative that the preferred arterial catheter would have relatively similar behavior to the PTFE arterial catheter during the initial placement by the practitioner. The results show the preferred tubing formed from hydrophilic polyurethane has a 5% modulus that is significantly lower after exposure to physiological conditions and is further reduced by the 4 hour exposure to the physiological conditions, while PTFE is substantially unchanged and not as compliant. Thus, the preferred arterial catheter of the invention is less likely to cause trauma to the blood vessel wall during an extended duration placement than the common PTFE arterial catheter.

TABLE 3

Bend force Softening Bend Force (gms)

| Time | Dry | Blood/37° C. |
|---|---|---|
| Hydrophilic polyurethane | | |
| 0 hr | 22.6 | 5.4 |
| 4 hr | | 6.8 |
| PTFE | | |
| 0 hr | 34.8 | 29.3 |
| 4 hr | | 33.4 |

Referring to Table 3, the test results show the Bend force for the hydrophilic polyurethane is originally somewhat lower than for PTFE and is substantially reduced by the exposure to physiological conditions, while the PTFE bend force is substantially unchanged by exposure to physiological conditions. Again, these results suggest that the arterial catheter of the invention is less likely to cause trauma to the patient's blood vessel. However, since the arterial catheter of the invention is much easier to bend and is more compliant, particularly after exposure time to physiological conditions, were it not for the presence of holes 30 and the interior projections 28 of the present invention, the bore of an arterial catheter formed from such a compliant material would easily be occluded by bending or by tip contact with the interior wall of the patient's blood vessel.

Figure 15:
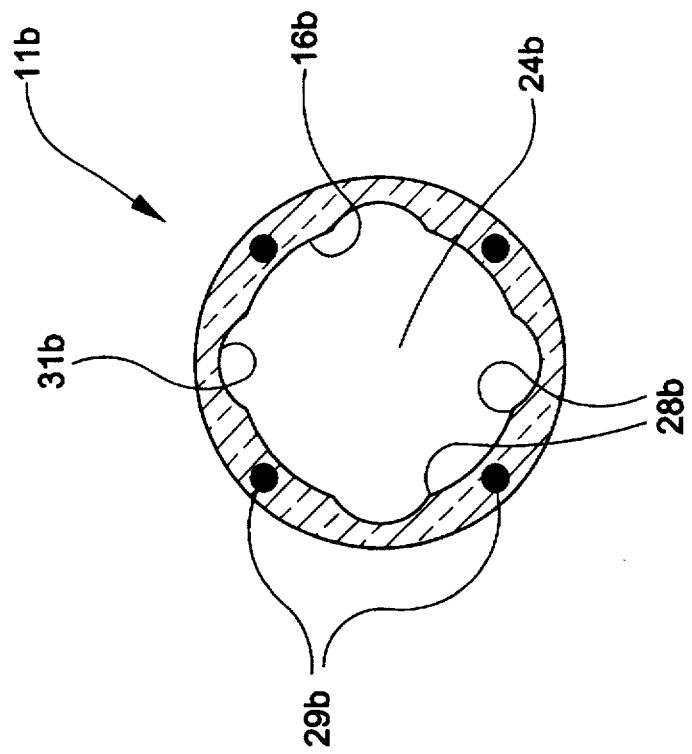
FIG. 15 is a lateral cross-sectional view of another embodiment of the arterial catheter of the present invention.
Figure 14:
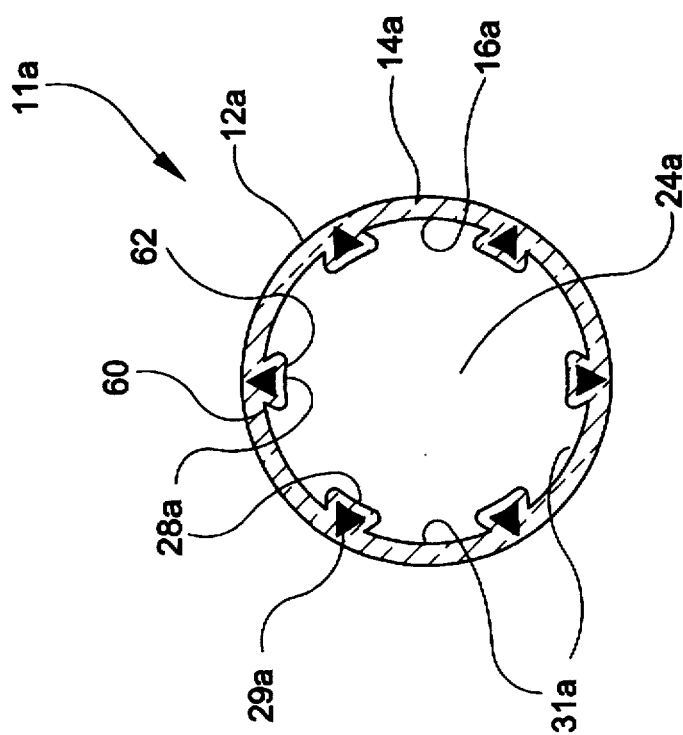
FIG. 14 is a lateral cross-sectional view of an embodiment of the arterial catheter of the present invention.

FIG. 4 illustrates a preferred cross-sectional configuration of the arterial catheter of the invention. As shown in FIG. 4, arterial catheter 11 has six inward projections 28, each projection being substantially rectangular and having a generally circular radiopaque stripe 29. The precise cross-sectional shape of projection 28 and the number and cross-sectional shape of radiopaque stripe 29 may be changed to fit requirements imposed by particular manufacturing and procedure requirement. Thus other cross-sectional shapes and numbers of projections 28 and radiopaque stripes 29 may be envisioned and are considered to be within the scope of the present invention. Referring to FIGS. 14 and 15, alternative embodiments for the configuration of the cross-section of the arterial catheter of the present invention is illustrated. In these alternative embodiments, the structure of the arterial catheter is substantially similar to the arterial catheter of FIGS. 1-7 and 10-13. Accordingly, substantially similar components that perform substantially similar functions are numbered identically to those components of the embodiments of FIGS. 1-6 except that suffixes "a" and "b" are used to identify those components in FIGS. 14 and 15 respectively.

As shown in FIG. 14, arterial catheter 11a has elongate tube 12a with sidewall 14a that has inside surface 16a.

Arterial catheter 11a has proximal end 18a, distal end 20a and hollow bore 24a therethrough with inside surface 16a. Surface 16a has a plurality of inward projections 28a disposed longitudinally from proximal end 18a to distal end 20a. Between projections 28a are spaces 31a. In this embodiment, projections 28a have a narrower base 60 where projection 28a joins inside surface 16a than a top surface 62. Additionally, radiopaque stripe 29a has a substantially triangular cross-section.

As shown in FIG. 15, arterial catheter 11b has elongate tube 12b with sidewall 14b that has inside surface 16b. Arterial catheter 11b has proximal end 18b, distal end 20b and hollow bore 24b therethrough with inside surface 16b. Surface 16b has a plurality of inward projections 28b disposed longitudinally from proximal end 18b to distal end 20b. In this embodiment, projections 28b have a more rounded configuration and the number of radiopaque stripes 29b does not correspond to the projections 28b. Spaces 31b are seen between the radiopaque stripes 29b.

In the embodiments illustrated in FIGS. 14 and 15, as well of those of FIGS. 1–7 and 10–13, when the catheter is flexed or bent, the inward projections are of sufficient size, preferably extending inwardly from the inside surface more than about 0.05 mm, and shaped to engage each other and maintain a fluid flow through the bore.

Figure 16:
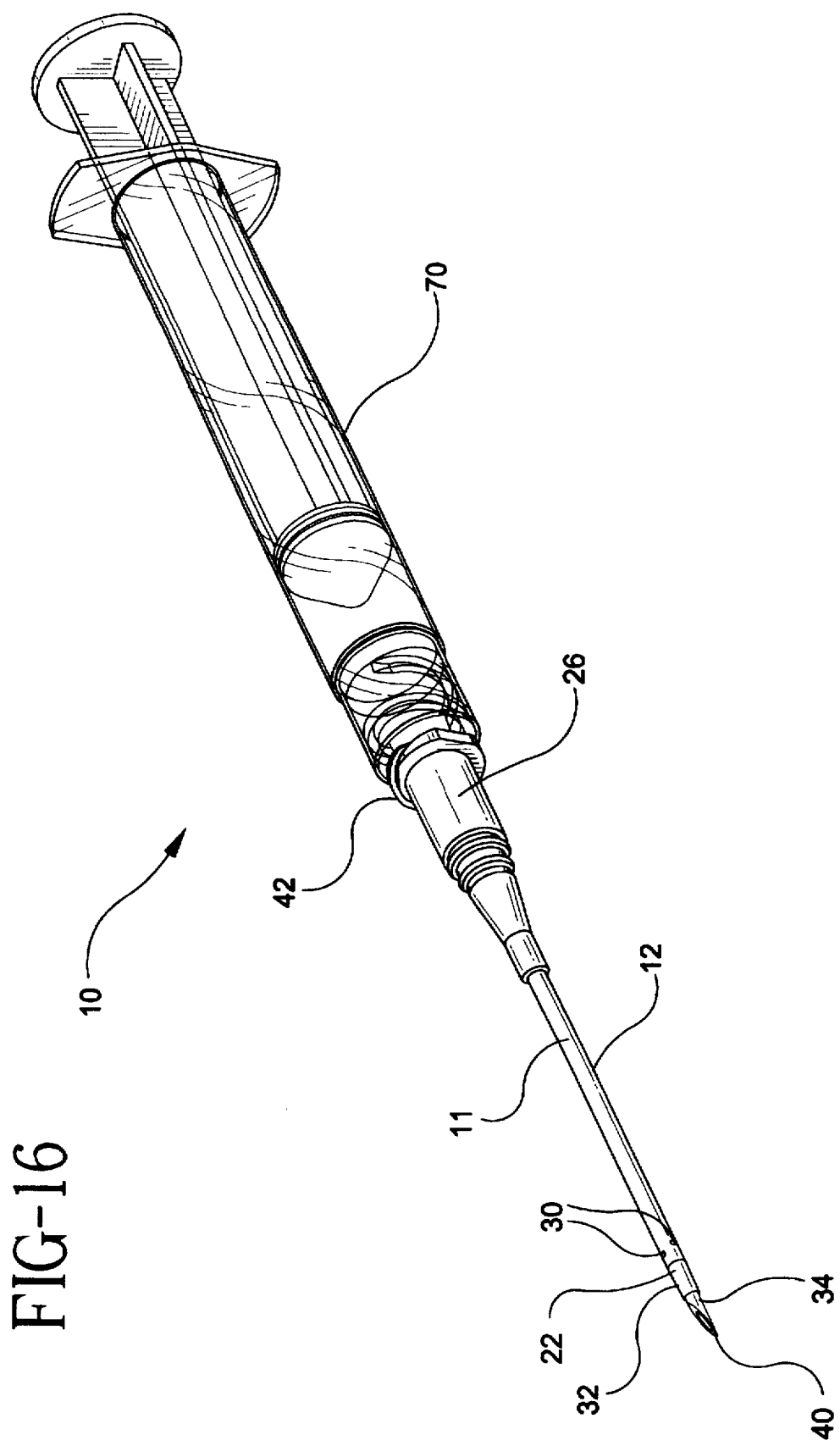
FIG. 16 is a perspective view of the arterial catheter assembly of the present invention mounted on a hypodermic syringe.

Referring to FIG. 16, for some applications, assembly 10 may include a syringe 70. A practitioner may prefer to insert assembly 10 with syringe 70 mounted on needle hub 42, using the syringe chamber to confirm the presence of arterial blood. The practitioner may then remove syringe 70 with the needle attached, occlude catheter hub 26 and then mount either a three-way valve or a PRN type device on the catheter hub.

The presence of inward projections on the inside wall of the bore of the catheter of the invention substantially reduces the possibility of occlusion of the bore when the catheter is bent, because as the bore is collapsed by bending, the inward projections interfere with each other and maintain a pathway for fluid flow. Additionally, the at least one hole through the sidewall provides a pathway for fluid to enter the bore if the tip is occluded. Prior arterial catheters generally are not formed from a soft material because the thin tip area is prone to collapse, either from suction or from bending, and substantially prevent fluid flow. In the present invention, while the formation of the tapered tip substantially diminishes the inward projections that keep the bore open, the holes in the sidewall of the present invention maintain fluid flow. The catheter of the invention is thus able to be formed from a softer material. The catheter of the invention thus substantially eliminates problems associated with damage to the blood vessel opposite the penetration site seen with catheters formed from stiffer materials and provides an advance to the art of arterial catheters.

What is claimed is:

1. An arterial catheter and inserter needle assembly comprising:

an arterial catheter comprising an elongate tube having a sidewall with an inside surface and an outside diameter, a proximal end, an open distal end having a tip portion and a hollow bore therethrough with an inside diameter, a hub attached to said proximal end in fluid communication with said hollow bore, said inside surface of said hollow bore having a plurality of inward projections disposed longitudinally from said proximal end to said distal end, said tip portion having at least one hole through said sidewall into said bore and comprising a taper of said sidewall outside diameter distally from said at least one hole to said open distal end, said inward projections in said bore being substantially diminished on said inside surface at said taper; and an elongate inserter needle disposed within the arterial catheter having a proximal end, a distal end, and a passageway therethrough sized to fit within said inside diameter of said bore of said arterial catheter, a hub attached at said proximal end of said needle sized to releasably fit within said hub of said arterial catheter, a sharpened point on said distal end of said needle, said needle having a sufficient length so that said sharpened point of said needle extends beyond said tapered tip portion of said catheter when said inserter needle is disposed within said bore of said catheter and said needle hub is positioned in said catheter hub.

2. The assembly of claim 1 wherein said catheter hub comprises a female luer fitting.

3. The assembly of claim 1 wherein said inserter needle hub comprises a male luer fitting.

4. The assembly of claim 3 further comprising a vented plug disposed in and sized to fit removably within said needle hub.

5. The assembly of claim 1 further including a syringe having a tip disposed in and sized to fit releasably into said arterial catheter hub and into said needle hub.

6. The assembly of claim 1 further including a shield disposed over and sized to releasably fit over said catheter and prevent inadvertent access to said catheter and said inserter needle distal sharpened point.

7. The assembly of claim 1 wherein said arterial catheter tip portion includes three holes in said sidewall, said holes having each having a diameter between about sixty to about seventy-five percent of said inside diameter of said hollow bore, said holes disposed about said sidewall about one hundred twenty degrees apart.

8. The assembly of claim 1 wherein said catheter has an outside diameter between about 0.7 mm to about 1.3 mm.

9. The assembly of claim 8 wherein said needle has an outside diameter between about 0.5 mm to about 1.0 mm.

10. The assembly of claim 9 wherein said catheter has an outside diameter about 0.9 mm, said needle having an outside diameter about 0.7 mm.

11. The assembly of claim 10 wherein said plurality of inward projections extend more than about 0.05 mm into said bore of said catheter.

12. An arterial catheter comprising:

an elongate tube having a sidewall with an inside surface and an outside diameter, a proximal end, an open distal end having a tip portion, and a hollow bore with an inside diameter therethrough;

a hub attached to said proximal end in fluid communication with said hollow bore;

said inside surface of said hollow bore having a plurality of inward projections disposed longitudinally from said proximal end to said distal end wherein at least one of said inward projections includes a radiopaque material and wherein said radiopaque material is incorporated in a thermoplastic polyester;

said tip portion having at least one hole through said sidewall into said bore and comprising a taper of said sidewall outside diameter distally from said hole to said open distal end, said inward projections in said bore being substantially diminished on said inside surface at said taper.

13. The arterial catheter of claim 12 wherein said sidewall includes a longitudinal space between each of said inward projections, and wherein at least one of said longitudinal spaces is at least translucent.

14. An arterial catheter comprising:

an elongate tube having a sidewall with an inside surface and an outside diameter, a proximal end, an open distal end having a tip portion, and a hollow bore with an inside diameter therethrough:

a hub attached to said proximal end in fluid communication with said hollow bore;

said inside surface of said hollow bore having a plurality of inward projections disposed longitudinally from said proximal end to said distal end;

said tip portion having three holes through said sidewall into said bore disposed about one hundred twenty degrees apart about said sidewall and comprising a taper of said sidewall outside diameter distally from said holes to said open distal end, said inward projections in said bore being substantially diminished on said inside surface at said taper and wherein a distance from said each hole to said open distal end is between about 2.8 to about 3.6 times said inside diameter.

15. The arterial catheter of claim 14 wherein each said distance from said each hole to said open distal end is not equal.

16. The arterial catheter of claim 14 wherein a diameter of said each hole is between about sixty to about seventy five percent of said inside diameter of said hollow bore.

17. An arterial catheter comprising:

an elongate tube having a sidewall with an inside surface and an outside diameter, a proximal end, an open distal end having a tip portion, and a hollow bore with an inside diameter therethrough, wherein said tube is formed by an extrusion process from a material comprising a hydrophilic thermoplastic polyurethane, said polyurethane having a lower five percent modulus after exposure to physiological conditions than the five percent modulus at ambient conditions and wherein said thermoplastic polyurethane is coextruded with a thermoplastic polyester having a radiopaque material incorporated therein, so that said polyester forms a radiopaque longitudinal stripe;

a hub attached to said proximal end in fluid communication with said hollow bore;

said inside surface of said hollow bore having a plurality of inward projections disposed longitudinally from said Proximal end to said distal end;

said tip portion having at least one hole through said sidewall into said bore and comprising a taper of said sidewall outside diameter distally from said hole to said open distal end, said inward projections in said bore being substantially diminished on said inside surface at said taper.

\* \* \* \* \*